(12) United States Patent
Boden et al.

(10) Patent No.: US 6,303,817 B1
(45) Date of Patent: Oct. 16, 2001

(54) METHOD FOR MAKING AMIDES

(75) Inventors: Richard M. Boden, Ocean; Carlos Ramirez, Dover, both of NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/636,045

(22) Filed: Aug. 10, 2000

(51) Int. Cl.$^7$ .................................................. C07C 231/06
(52) U.S. Cl. .................... 564/129; 564/124; 564/189; 564/215
(58) Field of Search ................................. 564/124, 129, 564/215, 189

(56) References Cited

U.S. PATENT DOCUMENTS

| | | |
|---|---|---|
| 3,644,613 | 2/1972 | Moeller et al. . |
| 3,793,446 | 2/1974 | Moeller et al. . |
| 3,793,463 | 2/1974 | Moeller et al. . |
| 3,830,930 | 8/1974 | Moeller et al. . |
| 4,029,759 | 6/1977 | Humbert et al. . |
| 4,032,661 | 6/1977 | Rowsell et al. . |
| 4,033,994 | 7/1977 | Watson et al. . |
| 4,044,120 | 8/1977 | Rowsell et al. . |
| 4,069,345 | 1/1978 | Gascoyne et al. . |
| 4,070,449 | 1/1978 | Rowsell et al. . |
| 4,070,496 | 1/1978 | Rowsell et al. . |
| 4,136,163 | 1/1979 | Watson et al. . |
| 4,136,164 | 1/1979 | Rowsell et al. . |
| 4,150,052 | 4/1979 | Watson et al. . |
| 4,153,679 | 5/1979 | Rowsell et al. . |
| 4,157,384 | 6/1979 | Watson et al. . |
| 4,178,459 | 12/1979 | Watson et al. . |
| 4,190,643 | 2/1980 | Watson et al. . |
| 4,193,936 | 3/1980 | Watson et al. . |
| 4,226,988 | 10/1980 | Watson et al. . |
| 4,296,093 | 10/1981 | Rowsell et al. . |
| 5,009,893 | 4/1991 | Cherukuri et al. . |
| 5,372,824 | 12/1994 | Record et al. . |

FOREIGN PATENT DOCUMENTS

| | | |
|---|---|---|
| 2064918 | 10/1992 | (CA) . |
| 06/510890 | 1/1994 | (JP) . |
| WO93/23005 | 11/1993 | (WO) . |

OTHER PUBLICATIONS

Journal of the Society of Cosmetic Chemists, 29, 185–200 (1978)—"New Compounds with the Menthol Cooling Effect".

*Primary Examiner*—Shailendra Kumar
(74) *Attorney, Agent, or Firm*—Joseph F. Leightner

(57) ABSTRACT

The invention relates to the manufacture of amide compounds provided through the reaction of nitrile compounds and a sulfate compound to form the related amide compound. In a preferred embodiment a diol or a triol is employed as a solvent, thereby increasing the yield of the product.

10 Claims, No Drawings

METHOD FOR MAKING AMIDES

FIELD OF THE INVENTION

The present invention relates to amides, more specifically a method of making butanamides in a new process.

BACKGROUND OF THE INVENTION

U.S. Pat. Nos. 4,153,679 and 4,226,988, hereby incorporated by reference, disclose the use of paramenthane and acyclic carboxarnides as having a cooling effect on the skin and mucous membranes. These patents disclose the preparation and separation of the compounds through a three-step reaction sequence. The steps basically involve the hydrolysis of the compounds to an acid. The acid product is then reacted with thionyl chloride to form an acid chloride. The acid chloride is then reacted with an alkylamine to form carboxy amide While this reaction is suitable for preparing the carboxamides, the process does not lend itself to the manufacture of the desired product in a simple economical process.

There is an ongoing need to provide the amides in high yield and in a simple, cost effective manner.

SUMMARY OF THE INVENTION

The invention a method for manufacturing amides of the formula

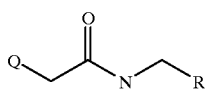

where Q is R

And where R is independently selected from hydrogen, $(C_1-C_{12})$alkyl, $(C_1-C_{12})$alkoxy, halo $(C_1-C_{12})$alkyl, halo $(C_1-C_{12})$alkoxy, $(C_2-C_{12})$alkenyl, halo$(C_2-C_{12})$alkenyl, $(C_2-C_{12})$alkynyl, halo$(C_2-C_{12})$alkynyl, $(C_1-C_{12})$alkoxy $(C_1-C_{12})$alkyl, $(C_1-C_{12})$alkoxy $(C_2-C_{12})$alkenyl, $(C_1-C_{12})$alkoxy $(C_2-C_{12})$alkynyl, $(C_2-C_{12})$alkenyl$(C_1-C_{12})$alkoxy, $(C_2-C_{12})$alkynyl$(C_1-C_{12})$alkoxy, $(C_2-C_{12})$alkynyl $(C_2-C_{12})$alkenyl, $(C_2-C_{12})$alkenyl$(C_2-C_{12})$alkynyl, $(C_3-C_7)$cycloalkyl, halo$(C_3-C_7)$cycloalkyl, $(C_3-C_7)$cycloalkyl $(C_1-C_{12})$alkyl, $(C_3-C_7)$cycloalkyl$(C_2-C_{12})$alkenyl, $(C_3-C_7)$cycloalkyl$(C_2-C_{12})$alkynyl, $(C_1-C_{12})$ alkyl$(C_3-C_7)$cycloalkyl, $(C_1-C_{12})$alkoxy$(C_3-C_7)$cycloalkyl, $(C_2-C_{12})$alkenyl$(C_3-C_7)$ cycloalkyl, $(C_2-C_{12})$alkynyl$(C_3-C_7)$cycloalkyl, halo$(C_1-C_{12})$alkyl $(C_3-C_7)$cycloalkyl, halo $(C_1-C_{12})$ alkoxy$(C_3-C_7)$cycloalkyl, halo$(C_2-C_{12})$alkenyl $(C_3-C_7)$cycloalkyl, halo$(C_2-C_{12})$ alkynyl$(C_3-C_7)$cycloalkyl, halo$(C_3-C_7)$alkenyl$(C_3-C_7)$cycloalkyl, halo $(C_2-C_{12})$ alkynyl$(C_3-C_7)$cycloalkyl, halo$(C_3-C_7)$alkenyl $(C_3-C_7)$cycloalkyl, $(C_1-C_{12})$ alkoxy$(C_1-C_{12})$alkyl $(C_3-C_7)$ cycloalkyl, halo$(C_3-C_7)$cycloalkyl$(C_3-C_7)$ cycloalkyl, $(C_1-C_{12})$alkoxy $(C_1-C_{12})$alkyl$(C_3-C_7)$cycloalkyl, $(C_1-C_{12})$ alkoxy $(C_2-C_{12})$alkenyl$(C_3-C_7)$ cycloalkyl, $(C_2-C_{12})$ alkenyl$(C_1-C_{12})$alkoxy $(C_3-C_7)$cycloalkyl, $(C_1-C_{12})$alkoxy $(C_2-C_{12})$alkynyl$(C_3-C_7)$ cycloalkyl, $(C_2-C_{12})$alkynyl $(C_1-C_{12})$alkoxy $(C_3-C_7)$cycloalkyl, $(C_2-C_{12})$alkenyl $(C_2-C_{12})$alkynyl$(C_3-C_7)$cycloalkyl, $(C_2-C_{12})$alkynyl $(C_2-C_{12})$alkenyl$(C_3-C_7)$cycloalkyl, $(C_3-C_7)$ cycloalkyl $(C_3-C_7)$ cycloalkyl, $(C_1-C_{12})$alkyl $(C_3-C_7)$cycloalkyl $(C_3-C_7)$cycloalkyl, $(C_2-C_{12})$alkynyl$(C_3-C_7)$cycloalkyl $(C_3-C_7)$cycloalkyl, $(C_2-C_{12})$alkenyl $(C_3-C_7)$cycloalkyl, $(C_1-C_{12})$alkoxy$(C_3-C_7)$ cycloalkyl $(C_3-C_7)$cycloalkyl, $(C_3-C_7)$ cycloalkyl $(C_1-C_{12})$alkyl $(C_3-C_7)$cycloalkyl, $(C_3-C_7)$cycloalkyl $(C_2-C_{12})$alkenyl $(C_3-C_7)$cycloalkyl, $(C_3-C_7)$cycloalkyl$(C_2-C_{12})$alkynyl $(C_3-C_7)$cycloalkyl, $(C_3-C_7)$ cycloalkyl$(C_1-C_{12})$alkoxy $(C_3-C_7)$cycloalkyl, $(C_3-C_7)$cycloalkyl $(C_3-C_7)$cycloalkyl $(C_3-C_7)$cycloalkyl, $(C_3-C_7)$cycloalkyl$(C_1-C_{12})$alkenyl $(C_3-C_7)$ cycloalkyl, $(C_3-C_7)$cycloalkyl$(C_1-C_{12})$alkoxy $(C_2-C_{12})$ alkenyl$(C_3-C_7)$cycloalkyl, aryl, aralkyl, aryl $(C_1-C_{12})$alkoxy, aryl$(C_2-C_{12})$alkenyl, aryl $(C_2-C_{12})$alkynyl, aryl$(C_3-C_7)$cycloalkyl, aryloxy$(C_1-C_{12})$alkyl, aryloxy $(C_2-C_{12})$alkynyl, aryloxy$(C_2-C_{12})$alkenyl, aryl $(C_1-C_{12})$alkoxy $(C_3-C_7)$cycloalkyl, aryl$(C_2-C_{12})$ alkenyl $(C_3-C_7)$ cycloalkyl, aryl$(C_2-C_{12})$alkynyl$(C_3-C_7)$ cycloalkyl, aryl$(C_3-C_7)$ cycloalkyl$(C_3-C_7)$cycloalkyl, $(C_3-C_7)$cycloalkylaryl, aryl$(C_1-C_4)$alkyl $(C_3-C_7)$ cycloalkyl,heterocyclic, aryl $(C_1-C_4)$alkylheterocyclic, aryl $(C_2-C_4)$alkylheterocyclic, aryl $(C_2-C_4)$alkynylheterocyclic, heterocyclic $(C_1-C_4)$alkyl, and heterocyclic $(C_3-C_7)$ cycloalkyl, $(C_1-C_6)$alkylphosphiny, $(C_1-C_6)$ alkylphosphonyl, $(C_1-C_6)$alkylphosphonate, $(C_1-C_6)$ alkylphosphite comprising:

Providing a nitrile compound of Formula II

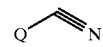

where Q is preferably

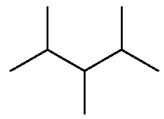

or

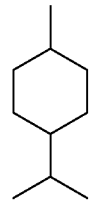

and Q can be as defined above
and reacting the nitrile compound with the compound of Formula Ill hereinbelow:

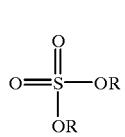

(III)

where R is defined above

More specifically, the present invention is directed to the preparation of N,2,3-trimethyl-2-isoethyl-menthylbutanamide by the reaction of dimethylsulfate and disopropylpropionylnitrile. Another embodiment of the invention is directed to the preparation of N-2,3-trimethyl-2-ethylbutanarnide by the reaction of menthyl nitrile with diethyl sulfate.

The present reaction provides yields of the amide in commercially acceptable yields, in a single reaction step. In a highly preferred embodiment, diol and triol esters are employed as a solvent which has been found to increase reaction yields. These and other embodiments of the present invention will become apparent upon referring to the following description of the invention.

DETAILED DESCRIPTION OF THE INVENTION

The present invention is based upon the discovery of a simple, efficient reaction to form the amide compounds recited herein. The preferred reaction products of the present invention are N-methyltrimethyl isopropyl butanamide and N-ethylmentyl carboxyamide. These amides are provided in a single reaction step by the reaction of a nitrile compound and a sulfate compound.

Suitable nitrile materials of formnula I include diisopropylpropionylnitrile, menthyl nitrile and the like.

The nitriles of Formula I are reacted with a sulfate compound of formula II, preferably selected from the group selected from dimethyl sulfate and diethyl sulfate.

The compounds of Formula I and II can be added in stoichiometric equal amounts. Preferably the level of dimethyl sulfate or diethyl sulfate is provided in stoichiometric excess so as to drive the reaction to higher yields of the resulting amide.

The aforementioned $(C_1-C_{12})$alkyl, $(C_1-C_{12})$alkoxy, $(C_2-C_{12})$alkenyl, $(C_2-C_2)$alkynyl and $(C_3-C_7)$cycloalkyl groups may be optionally substituted with up to three substituents selected from the group consisting of nitro, trihalomethyl and cyano.

The term "alkyl" includes both branched and straight chain alkyl groups from 1 to 12 carbon atoms. Typical alkyl groups are methyl, ethyl, n-propyl, isopropyl, n-butyl, sec-butyl, isobutyl, t-butyl, n-pentyl, isopentyl, n-hexyl, n-heptyl, isooctyl, nonyl, decyl, undecyl, dodecyl and the like. The term "haloalkyl" refers to an alkyl group substituted with 1 to 3 halogens.

The term "alkoxy" includes both branched and straight chain alkyl groups from 1 to 12 carbon atoms containing at least one oxygen atom. Typical alkoxy groups are methoxy, ethoxy, n-propoxy, isopropoxy, n-butoxy, sec-butoxy, isobutoxyl, t-butoxy, n-pentoxy, isopentoxy, n-hexoxy, n-heptoxy and the like. The term "haloalkoxy" refers to an alkoxy group substituted with 1 to 3 halogens.

The term "alkenyl" refers to an ethylenically unsaturated hydrocarbon group, straight or branched, having a chain length of 2 to 12 carbon atoms and 1 to 2 ethylenic bonds. The term "haloalkenyl" refers to an alkenyl group substituted with 1 to 3 halogen atoms.

The term "alkynyl" refers to an unsaturated hydrocarbon group, straight or branched, having a chain length of 2 to 12 carbon atoms and 1 to 2 acetylenic bonds. The term "halokynyl" refers to an alkynyl group substituted with 1 to 3 halogens.

The term "cycloalkyl" refers to a saturated ring system having 3 to 7 carbon atoms.

The term "aryl" includes phenyl or naphthyl, which may be substituted with up to three substituents independently selected from the group consisting of halogen, cyano, nitro, phenyl, phenoxy, $(C_1-C_6)$alkyl, $(C_1-C_4)$alkylthio, $(C_1-C_4)$alkylsulfoxide, $(C_1-C_6)$alkoxy, and halo $(C_1-C_4)$ alkyl.

Typical aryl substituents include, but are not limited to, 4-chlorophenyl, 4-fluorophenyl, 4-bromophenyl, 2-methoxyphenyl, 2-methylphenyl, 3-methylphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term "heterocyclic" refers to a substituted or unsubstituted 5 to 6 membered unsaturated ring containing one, two or three heteroatoms, preferably one or two heteroatoms independently selected from oxygen, nitrogen and sulfur, or to a bicyclic unsaturated ring system containing up to 10 atoms including one heteroatom selected from oxygen, nitrogen and sulfur. Examples of heterocycles include, but are not limited to, 2-, 3-, or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from $(C_1-C_2)$ alkyl, halogen, cyano, nitro and trihalomethyl.

The term "aralkyl" is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl and 4-methylbenzyl. Typical phenethyl moieties are 2-(chlorophenyl)ethyl, 2-(3-chlorophenyl) etbyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-phenyl)ethyl, 2-(4-methylphenyl)ethyl, 2-(4-trifluoromethylphenyl)ethyl, 2-(2methoxyphenyl)ethyl, 2-(3-methoxyphenyl) ethyl, 2-(4-methoxyphenyl)ethyl, 2-(2,4-dichlorophenyl)ethyl, 2-(3,5-dimethoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyi)propyl, 3-(3-fluorophenyl) propyi, 3-(4-fluorophenyl)propyl, 3-(2-methylphenyl)propyl, 3 -(3-methylphenyl)propyl, 3 -(4-methylphenyl)ethyl, 3-(2-methoxyphenyl)propyl, 3-(3-nmethoxyphenyl)propyl, 3-(4-methoxyphenyl) propyl, 3-(4-trifluoromethylphenyl)propyl, 3-(2,4-dichlorophenyl)propyl and 3-3,5-dimethoxyphenyl) propyl.

Typical phenbutyl moieties include 4-phenylbutyl, 4-(2-chlorophenyl)butyl, 4-(3-chlorophenyl) butyl, 4-(4-chlorophenyl)butyl, 4-(2-fluorophenyl)butyl, 4-(3-fluorophenyl) butyl, 4-(4-fluorophenyl) butyl, 4-(2-methylphenyl)butyl, 4-(3-methylphenyl)butyl, 4-(4-methylphenyl)butyl, 4-(2,4-dichlorophenyl)butyl, 4-(2-methoxyphenyl)butyl, 4-(3 -methoxyphenyi)butyl and 4-(4-methoxyphenyl) butyl.

Halogen or halo is meant to include iodo, fluoro, bromo and chloro moieties.

The reaction temperature is from about 120 to about 165° C.; preferably from about 130 to about 155 and most preferably from 135 to about 150° C.

In a preferred embodiment of the present invention, a solvent system is employed. The Solvent is selected from various diol and triol esters and mixtures of these materials.

The diol esters have the structure of Formula IV

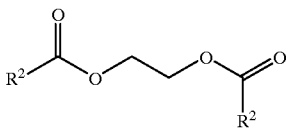
(IV)

And triol esters of the structure presented in Formula V

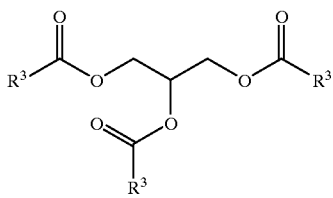
(V)

Where $R^2$ is H or $(C_1-C_{18})$alkyl; and $R^3$ is H or $(C_1-C_{18})$alkyl.

Suitable solvent materials include triacetin, propylene glycol acetate, ethylene glycol acetate, 1,2,6-hexanetriol acetate and the like. Preferably the molar ratio of solvent to nitrile is greater than about 1.25/1; preferably greater than 1.5/1 and most preferably greater than 1.75/1. For example, a preferred the level of triacetin is 1.5 times the stoichiometric level of diisopropylpropionitrile provided in a reaction with dimethyl sulfate.

The present invention is sufficient to provide yields of greater than 50 mole % based upon the level of nitrile present. Yields of greater than about 60 mole percent and preferably greater that about 70 mole percent are also possible with the present reaction.

It has surprisingly been found that the incorporation of the mono, diol and triol esters as the solvent allows for higher yields and better reaction times. Reactions conducted without the diol or triol ester solvent provided much lower yields and much longer reaction times. The invention will now be illustrated by the following example.

Example 1

Preparation of Trimethyl Isopropyl Butanamide

Diisopropylproprionitrile (200 grams) and triacetin (1000 grams) were charged to a 5 liter reaction reactor equipped with a mechanical stirrer, condenser, and heating mantle. The reactor contents are heated to 145 C. Dimethyl sulfate (344 grams) is fed into the reactor while recovering methyl acetate. The batch is allowed to continue until no more methyl acetate is recovered. The approximate reaction time was about 5 hours.

The contents of the reactor were then allowed to cool to room temperature and ethyl acetate is added to reduce the viscosity of the product. The batch is then decomped into 25% caustic. The crude is washed twice with salt water. The crude is then distilled.

This procedure yielded approximately 70% mole/mole based on the charged amount of diisopropylproprionitrile.

What is claimed is:
1. A method for producing an amide of the formula

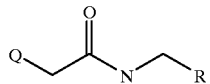

where Q is

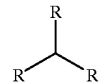

Comprising reacting a nitrile of Formula II

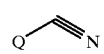
(II)

where Q is defined above;
and reacting said compound with a compound of Formula III, $$O=\overset{O}{\underset{OR}{S}}-OR$$
(III)

where R is
independently selected from hydrogen, $(C_1-C_{12})$alkyl, $(C_1-C_{12})$alkoxy, halo$(C_1-C_{12})$alkyl, halo $(C_1-C_{12})$alkoxy, $(C_2-C_{12})$alkenyl, halo$(C_2-C_{12})$alkenyl, $(C_2-C_2)$alkynyl, halo$(C_2-C_{12})$alkynyl, $(C_1-C_{12})$alkoxy$(C_1-C_{12})$alkyl, $(C_1-C_{12})$alkoxy$(C_2-C_{12})$alkenyl, $(C_1-C_{12})$alkoxy$(C_2-C_{12})$alkynyl, $(C_2-C_{12})$alkenyl$(C_1-C_{12})$alkoxy, $(C_2-C_{12})$alkynyl $(C_1-C_{12})$alkoxy, $(C_2-C_{12})$alkynyl$(C_2-C_{12})$alkenyl, $(C_2-C_{12})$alkenyl$(C_2-C_{12})$alkynyl, $(C_3-C_7)$cycloalkyl, halo $(C_3-C_7)$cycloalkyl, $(C_3-C_7)$cycloalkyl $(C_1-C_{12})$alkyl, $(C_3-C_7)$cycloalkyl$(C_2-C_{12})$alkenyl, $(C_3-C_7)$cycloalkyl $(C_2-C_{12})$alkynyl, $(C_1-C_{12})$alkyl $(C_3-C_7)$cycloalkyl, $(C_1-C_{12})$alkoxy$(C_3-C_7)$cycloalkyl, $(C_2-C_{12})$alkenyl $(C_3-C_7)$ cycloalkyl, $(C_2-C_{12})$alkynyl $(C_3-C_7)$cycloalkyl, halo$(C_1-C_{12})$alkyl$(C_3-C_7)$cycloalkyl, halo$(C_1-C_{12})$alkoxy $(C_3-C_7)$cycloalkyl, halo$(C_2-C_{12})$alkenyl$(C_3-C_7)$cycloalkyl, halo$(C_2-C_{12})$alkynyl$(C_3-C_7)$cycloalkyl, halo$(C_3-C_7)$ alkenyl $(C_3-C_7)$cycloalkyl, $(C_1-C_{12})$alkoxy$(C_1-C_{12})$alkyl $(C_3-C_7)$cycioalkyl, halo $(C_3-C_7)$cycloalkyl$(C_3-C_7)$ cycloalkyl, $(C_1-C_{12})$alkoxy$(C_1-C_{12})$alkyl $(C_3-C_7)$ cycloalkyl, $(C_{1\ -C12})$ alkoxy$(C_2-C_{12})$alkenyl$(C_3-C_7)$ cycloalkyl, $(C_2-C_{12})$alkenyl $(C_1-C_{12})$alkoxy$(C_3-C_7)$ cycloalkyl, $(C_1-C_{12})$alkoxy$(C_2-C_{12})$alkynyl$(C_3-C_7)$ cycloalkyl, $(C_2-C_{12})$alkynyl$(C_1-C_{12})$alkoxy$(C_3-C_7)$ cycloalkyl, $(C_2-C_{12})$alkenyl$(C_2-C_{12})$alkynyl$(C_3-C_7)$ cycloalkyl, $(C_2-C_{12})$alkynyl$(C_2-C_{12})$alkenyl $(C_3-C_7)$ cycloalkyl, $(C_3-C_7)$cycloalkyl$(C_3-C_7)$ cylcoalkyl, $(C_1-C_{12})$ alkyl$(C_3-C_7)$cycloalkyl $(C_3-C_7)$cycloalkyl, $(C_2-C_{12})$ alkenyl$(C_3-C_7)$cycloalkyl $(C_3-C_7)$cycloalkyl, $(C_2-C_{12})$ alkynyl$(C_3-C_7)$cycloalkyl$(C_3-C_7)$cycloalkyl, $(C_1-C_{12})$ alkoxy$(C_3-C_7)$ cycloalkyl $(C_3-C_7)$cycloalkyl, $(C_3-C_7)$ cycloalkyl$(C_1-C_{12})$alkyl$(C_3-C_7)$cycloalkyl, $(C_3-C_7)$ cylcoalkyl $(C_2-C_{12})$alkenyl$(C_3-C_7)$ cycloalkyl, $(C_3-C_7)$ cycloalkyl$(C_2-C_{12})$alkynyl$(C_3-C_7)$cycloalkyl, $(C_3-C_7)$ cycloalkyl$(C_1-C_{12})$alkoxy $(C_3-C_7)$cycloalkyl, $(C_3-C_7)$ cycloalkyl($C_3$–$C_7$)cycloalkyl($C_3$–$C_7$)cycloalkyl, ($C_3$–$C_7$) cycloalkyl($C_1$–$C_{12}$)alkenyl($C_3$–$C_7$)cycloalkyl, ($C_3$–$C_7$) cycloalkyl ($C_1$–$C_{12}$)alkoxy($C_2$–$C_{12}$) alkynyl($C_3$–$C_7$) cycloalkyl, aryl, aralkyl, aryl($C_1$–$C_{12}$)alkoxy, aryl($C_2$–$C_{12}$) alkenyl, aryl($C_2$–$C_{12}$) alkynyl, aryl($C_3$–$C_7$)cycloalkyl, aryloxy($C_1$–$C_{12}$)alkyl, aryloxy($C_2$–$C_{12}$) alkynyl, aryloxy ($C_2$–$C_{12}$) alkenyl, aryl($C_1$–$C_{12}$)alkoxy($C_3$–$C_7$)cycloalkyl, aryl($C_2$–$C_{12}$)alkenyl ($C_3$–$C_7$)cycloalkyl, aryl($C_2$–$C_{12}$) alkynyl($C_3$–$C_7$)cycloalkyl, aryl($C_3$–$C_7$)cycloalkyl($C_3$–$C_7$) cycloalkyl, ($C_3$–$C_7$)cycloalkylaryl, aryl($C_1$–$C_4$)alkyl ($C_3$–$C_7$)cycloalkyl, heterocyclic, aryl($C_1$–$C_4$) alkylheterocyclic, aryl($C_2$–$C_4$) alkenylheterocyclic, aryl ($C_2$–$C_4$)alkynylheterocyclic, heterocyclic ($C_1$–$C_4$)alkyl, and heterocyclic ($C_3$–$C_7$)cycloalkyl ($C_1$–$C_6$)alkylphosphinyl, ($C_1$–$C_6$)alkylphosphonyl, ($C_1$–$C_6$) alkylphosphonate, ($C_1$–$C_6$)alkylphosphite.

2. The method of claim 1 wherein a solvent is employed.

3. The method of claim 2 wherein the solvent is selected from diol esters, triol esters and mixtures thereof.

4. The method of claim 3 wherein the solvent is selected from a diol ester has a structure of Formula IV:

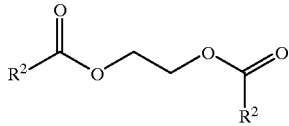

(IV)

And triols of the structure presented in Formula V

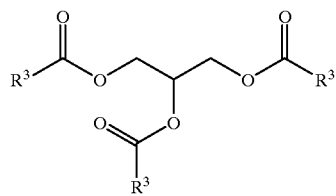

(V)

where $R_2$ is selected from H and ($C_1$–$C_{15}$)alkyl;
and $R_3$ is selected from H and ($C_1$–$C_{18}$)alkyl.

5. The method of claim 1 wherein the sulfate is dimethyl sulfate.

6. The method of claim 6 wherein the nitrile is diisopropionylnitrile.

7. The method of claim 6 wherein the amide is trimethylisopropylbutanamide.

8. The method of claim 1 wherein the yield is greater than about 50 mole percent.

9. The method of claim 4 wherein the solvent is selected from the group consisting of triacetin, propylene glycol acetate, ethylene glycol acetate, and 1,2,6-hexanetriol acetate.

10. The method of claim 1 wherein Q is selected from the group consisting of

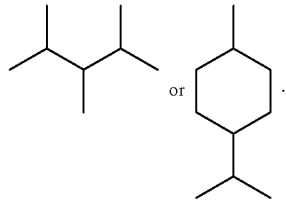

* * * * *